United States Patent [19]

Tu et al.

[11] Patent Number: 5,024,671

[45] Date of Patent: Jun. 18, 1991

[54] MICROPOROUS VASCULAR GRAFT

[75] Inventors: Roger Tu, Lake Forrest; David Chen, Irvine; Wilfred F. Mathewson, Dana Point, all of Calif.

[73] Assignee: Baxter International Inc., Deerfield, Ill.

[21] Appl. No.: 246,578

[22] Filed: Sep. 19, 1988

[51] Int. Cl.⁵ ............................................. A61F 2/06
[52] U.S. Cl. ......................................... 623/1; 623/12; 623/66
[58] Field of Search ............................... 623/1, 66, 12

[56] References Cited

U.S. PATENT DOCUMENTS

| | | | |
|---|---|---|---|
| 3,765,414 | 10/1973 | Arlen | 623/66 |
| 3,953,566 | 4/1976 | Gore | |
| 4,323,525 | 4/1982 | Bornat | |
| 4,355,426 | 10/1982 | MacGregor | |
| 4,475,972 | 10/1984 | Wong | |
| 4,583,969 | 4/1986 | Mortensen | 623/66 |
| 4,664,669 | 5/1987 | Ohyabu et al. | 623/66 |
| 4,770,852 | 9/1988 | Takahara et al. | 623/66 |

FOREIGN PATENT DOCUMENTS

| | | | |
|---|---|---|---|
| 0058275 | 8/1982 | European Pat. Off. | 623/12 |
| 0095940 | 1/1983 | European Pat. Off. | |
| 0299381 | 1/1989 | European Pat. Off. | 623/12 |
| 2553674 | 4/1985 | France | 623/12 |
| 2115776 | 3/1982 | United Kingdom | |

OTHER PUBLICATIONS

Annis, Bornat, Edwards, Higham, Loveday and Wilson; An Elastomeric Vascular Prosthesis; vol. XXIV, Trans. Am. Soc. Artif. Intern. Organs, 1978, pp. 209-214.

Primary Examiner—Randall L. Green
Assistant Examiner—Stephanie L. Jantorno
Attorney, Agent, or Firm—Michael C. Schiffer

[57] ABSTRACT

A vascular graft at least partially formed from porous hollow fibers, with at least some of the porous hollow fibers being located adjacent an inner surface of the vascular graft. The vascular grafts of the invention have a relatively small pore size for promoting tissue growth while inhibiting bleeding during the healing process. The porous hollow fibers used to form the vascular grafts of the invention further provide a storage situs for temporarily holding a drug or other material for delivery into the blood stream during the healing process. This storage capability may also be used for holding an inert gas while providing the graft with greater resiliency and cushioning characteristics than achievable with presently available vascular grafts.

30 Claims, 1 Drawing Sheet

MICROPOROUS VASCULAR GRAFT

BACKGROUND OF THE INVENTION

The present invention relates to porous vascular grafts. More particularly, the present invention relates to a porous vascular graft having its innermost surface formed from porous hollow fibers. The porous hollow fibers enhance the ingrowth of endothelial cells which promotes healing of the graft, and as a result ensures the assimilation of the graft into the body.

Vascular grafts are widely used to replace damaged or diseased veins and arteries. Vascular grafts are generally porous to promote the ingrowth of tissue during the healing process. There are numerous types of porous vascular grafts. One particular type of porous vascular graft is formed from a fluoropolymer, and specifically a polytetrafluoroethylene (PTFE) hollow body.

Fluoroplastics, such as polytetrafluoroethylene, are particularly advantageous for preparing vascular grafts because of their chemical inertness. The porous graft is created by expanding a formed fluoroplastic body, typically by stretching the body. The expanded or stretched fluoroplastic, and in particular PTFE body is characterized by a unique microporous node and fibril structure, see U.S. Pat. No. 3,953,566, Apr. 27, 1976 for more detail. While such expanded PTFE bodies possess some of the characteristics desirable for vascular grafts, the fabrication of the porous prosthetic grafts can be somewhat problematic. The problem of using fluoroplastics for vascular grafts is due to the fact of the considerable difficulty in making an article porous, and keeping it so, yet providing it with adequate strength.

Complicated, expensive processes have been devised to achieve porosity, yet retain strength. Such processes include, for example, adding a leachable material to the PTFE prior to forming, and subsequently leaching the material out of the formed article with a solvent.

The chemical inertness of fluoroplastics, such as PTFE, although a very desirable property, can be disadvantageous in some respects. For example, many materials are not compatible or miscible with PTFE, thus blending other property-enhancing materials with PTFE can be difficult. This incompatibility may cause, for example, delamination or bleeding of blended materials.

Additionally, processing of fluoropolymers has proved problematic due to their high molecular weight and melt viscosity. Certain fluoroelastomers, including poly-(tetrafluoroethylene-co-propylene). disclosed in U.S. Pat. No. 4,463,144, have a high molecular weight and hence can only be extruded with difficulty. Thus researchers have sought other materials from which vascular grafts may be formed.

Another type of porous vascular graft is one formed from one or more polymeric fibers wound about a mandrel. These fibers are wound in such a manner to form a solid structure in which the pores are defined as the spacing between adjacent fibers. Generally, this type of graft is formed from numerous fibers wound in a selected pattern about the mandrel. The advantage of this type of vascular graft is that the polymer composition from which the individual fibers are prepared can be selected to achieve different physical and chemical characteristics.

There are numerous methods of preparing vascular grafts from individual fibers. One particular method for preparing a synthetic porous vascular graft from individual fibers involves the electrostatic spinning of an organic polymer fiber about a rotating mandrel. This type of method is taught in European Patent Publication 95940. The spun fibers bind to one another with the porous structure being defined by the interconnected openings between the adjacent fibers. The porosity of the graft can be controlled by varying the mandrel rotating speed as the fibers are being wound about the mandrel.

Similar processes for preparing porous vascular grafts involving the spinning of fibers about an electrostatically charged mandrel are described in Annis, et al. (Transaction ASAIO, Vol. 24 1978) and U.S. Pat. No. 4,323,525. In the former process the fibers are formed by discharging a fiber forming polymer, in solution, from nozzles directed at the spinning mandrel. The electrostatic charge promotes the attraction of the fibers to the mandrel. The later process includes the use of a mandrel composed of a core and a removable sheath. The removable sheath promotes the ease of removing the formed fibrous tube.

U.S. Pat. No. 4,475,972 describes a process for preparing a vascular graft by winding polymeric fibers on a mandrel without electrostatic spinning. The overlying fibers are simultaneously bonded together. In this process, the porosity is created by varying the diameter of the fibers and the winding angles. A similar process is disclosed in Great Britain Patent Application No. 2115776, with the wound fibers bonded together using an adhesive or heat treatment. U.S. Pat. No. 4,355,426 describes a small pore flexible vascular graft having a luminal pore surface in fluid flow communication with the network of interconnected sphere-like pores.

While the above described vascular grafts provide adequate pore size to promote growth of tissue during the healing process, the pore structure of such grafts is relatively large. The relatively large pore structure promotes bleeding, that is the passage of the blood through the graft. This causes the potential of the retention of red blood cells within the graft. Further, large pore openings in a graft usually promote collagenous tissue ingrowth which may render the graft inflexible. This disadvantage with the pore size of presently available vascular grafts is particularly acute during the initial healing stages after the implantation. Specifically, the relatively large pore size reduces the potential of a satisfactory healing due to this potential of bleeding.

Another disadvantage with presently available vascular grafts concerns the luminal or inner graft surface. In accordance with conventional techniques, such as taught in U.S. Pat. No. 4,475,972, the resulting graft luminal surface is relatively rough and loose surface. Even with electrostatic spinning the inner surface of the graft can be rough and so porous so as to entrap various blood elements, leading to undesired acute thrombosis.

It would also be advantageous if presently available vascular grafts include the ability of providing a direct delivery of various types of drugs to the suture site. That is, if vascular grafts were constructed in some fashion to be able to temporarily store and then release a drug, e.g. an anticoagulant, into the blood. This could be useful in promoting the healing process, or eliminating the undesired thrombogenicity.

SUMMARY OF THE INVENTION

The present invention overcomes the above described disadvantages by providing a vascular graft having relatively small pore size to promote favorable tissue growth while inhibiting bleeding during the healing process. The vascular grafts of the invention further include a storage capability for temporarily holding a drug or other material for delivery into the blood stream during the healing process. This storage capability may also be used for holding an inert gas to provide the graft with greater resiliency and cushioning characteristics than achievable with presently available vascular grafts.

The implantable vascular graft of the invention possesses relatively small pore size by forming the graft at least partially from porous hollow fibers. Some of the porous hollow fibers are located adjacent the inner surface of the vascular graft. The porous hollow fibers which possess small pores are thus partitioned adjacent the blood contacting surface of the vascular graft. In comparison, the porosity of presently available grafts is provided by controlling the spacing between adjacent fibers. This is not only difficult to control but does not allow for the preparation of grafts with relatively small pore size.

The implantable vascular grafts of the invention will, in accordance with a preferred embodiment, be formed with a porous hollow fiber inner layer. This ensures that the greatest porosity is located directly adjacent the blood pathway through the graft, thus promoting the neointimal coverage at the blood contact lumen surface of tissue during the healing process. The inner layer of the vascular graft is then overlaid with additional solid of porous hollow fibers wound.

The porous hollow fibers provide for an increase in the overall porosity of the graft, while minimizing the size of the individual pores. The hollow fibers also provide a receptacle for holding, and gradually releasing drug or other compositions into the blood stream.

DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE INVENTION

The present invention is directed to vascular grafts and more specifically to vascular grafts formed from porous hollow fibers, either alone or in combination with solid fibers. The hollow fibers are generally positioned adjacent the interior, blood contacting surface of the graft. The use of porous hollow fibers provides the graft with a greater overall porosity than achievable with solid fibers, while minimizing the overall pore size. By positioning the hollow fibers adjacent to the blood stream the resulting increase in graft porosity facilitates the healing process. That is, the resulting graft has an increase in porosity at a location to allow for an increase in the tissue ingrowth and the neointimal development. This increase in tissue ingrowth and the neointimal development promotes the healing process in comparison with presently available grafts. A further benefit of using porous hollow fibers, and the positioning of such hollow fibers in close proximity to the blood stream is the ability to deliver drugs directly into the blood stream.

Figure 1:
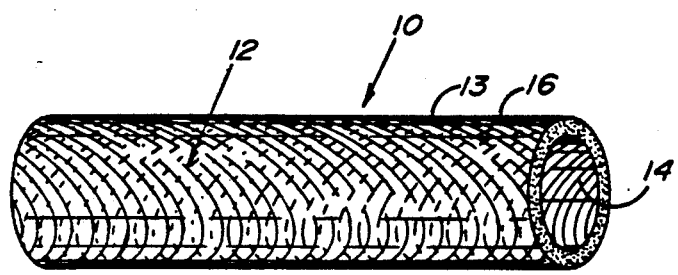
FIG. 1 is a prospective side view of a vascular graft prepared in accordance with an embodiment of the invention the instant invention.

Referring to FIG. 1 a vascular graft in accordance with an embodiment of the invention is seen generally at 10. The illustrated vascular graft 10 is basically an elongated hollow conduit 12. The conduit 12 includes an inner surface 14 and an opposing outer surface 16. The inner surface 14 defines the passageway through which the blood will flow. The conduit 12 is prepared from numerous fibers, one of which is indicated generally at 13, which are arranged in any pattern about the conduit 12. The conduit 12 is prepared by any suitable method, but generally involves winding one or more fibers 13 about a mandrel in accordance with a procedure to be more specifically discussed below.

Figure 2:
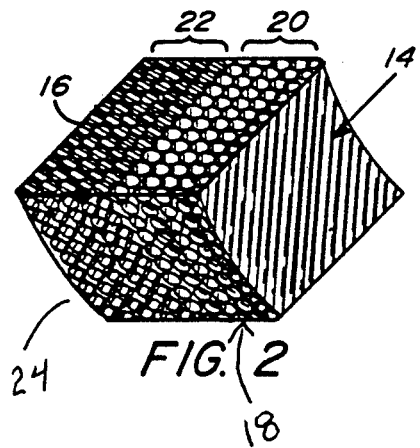
FIG. 2 is an enlargement of a cross-sectional view of a sliced section of the graft of FIG. 1.

Referring now to FIG. 2, an enlarged view of a section of the conduit 12 is seen. This conduit 12 section illustrates the positioning of the numerous fiber strands 13 which make up the conduit 12. The fiber strands 13 define the inner surface 14 and outer surface 16. As stated, the innermost layer of the conduit 12 is comprised of hollow fibers, one of which is seen at 18. The porous hollow fibers 18 may merely be positioned along this inner surface 14, or be used to construct the entire conduit 12. More specifically, the conduit 12 is formed with an inner layer of the hollow fibers 18, which layer is seen generally at 20, and second outer layer 22 is disposed about this first layer 20. The second layer 22 may be comprised of a plurality of solid fibers, one of which is seen generally at 24, or additional hollow fibers, not shown.

The conduit 12 is formed by winding the hollow fibers 18 or solid fibers 24, about a mandrel until a desired thickness of the respective inner and outer layers 20 and 22 are obtained. The entire structure may be held together using either an adhesive or by sintering, melting or solvating the various hollow fibers together.

The thickness of the two different layers 20 and 22 are not critical to the invention but generally, the inner layer 20 of hollow fibers 18 is sufficiently thick enough for the intended purpose. As stated the graft 10 of the invention is advantageously formed from porous hollow fibers to increase the porosity of the graft 10 and to provide a situs for containing one or more drugs or other chemicals for delivery into the blood stream. If the intended purpose of using the porous fibers 18 is to increase the necessary porosity of the graft 10, which as stated promotes healing by allowing for tissue-ingrowth, and neointimal development then the hollow fibers 18 layer 20 need not be that thick, that is, from about 20 microns to about 100 microns. If, however, the hollow fibers 18 are also to be used as a situs for drug storage, then the thickness of the layer 20 should be sufficiently large enough to provide the necessary capacity. Typically, the thickness of layer 20 will then be from about 50 microns to about 500 microns.

The solid fibers may be formed from any conventional crystalline polymer, but preferentially are formed from polytetrafluoroethylene (PTFE) or an elastomeric, polytetrafluoroethylene blend. The porous hollow fibers may also be formed from any suitable polymeric material. Generally, the hollow fibers are formed from semicrystalline or crystalline polymers, e.g. polyolefins and in particular polypropylene, polytetrafluoroethylene or an elastomeric-polytetrafluoroethylene blend.

The hollow fibers are prepared in accordance with standard extrusion techniques, with the desired polymer mixture being extruded through a die to form a hollow fiber having an inner and outer diameter, as required for the desired end use. If the graft 10 is to be used for drug delivery larger diametered fibers may be useful. However, the diameters of the fibers should be minimized to allow for the production of grafts 10 having a desired internal and external diameter, which limits the thickness of the inner and outer layer and thus the fibers. The grafts 10 are typically formed with an inner diameter of from 2 mm to about 10 mm, and an outer diameter of from about 2.3 mm to about 14 mm.

The porosity of the hollow fibers will depend upon the desired purpose for the graft 10. Generally, this porosity will be from about 30% to about 90%, and more preferably from about 40% to about 70%. The porous hollow fibers are prepared in accordance with standard techniques. For example, the hollow fibers may be stretched a given percentage in accordance with the techniques disclosed in U.S. Pat. No. 4,000,000, issued to Kamada or in accordance with the various techniques taught in *SYNTHETIC POLYMERIC MEMBRANES A STRUCTURAL PERSPECTIVE*, 2ND ED., Robert E. Kesting, Wiley & Sons, Inc. (1985), section 8.2 pages 290–297, both of which references are incorporated herein. Other suitable techniques for preparing porous hollow fibers useful for the preparation of the vascular grafts of the invention are disclosed in the above referenced text entitled *SYNTHETIC POLYMERIC MEMBRANES*, and in particular section 8.3 and in the entire Section 7 entitled PHASE-INVERSION MEMBRANES, all of which are incorporated herein by reference.

Figure 3:
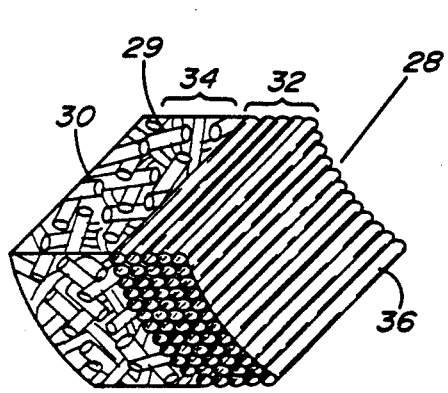
FIG. 3 is a prospective side view of a vascular graft in accordance with a second embodiment of the invention.
Figure 4:
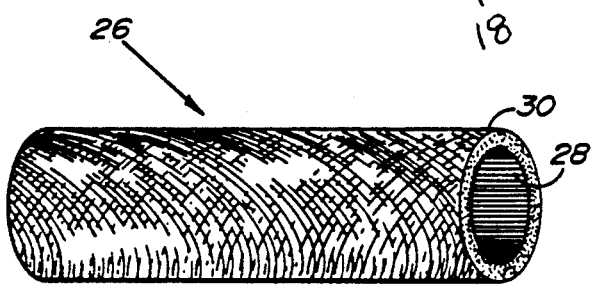
FIG. 4 is an enlargement of a cross-sectional view of a sliced section of the graft of FIG. 3.

Referring now to FIGS. 3 and 4, a vascular graft in accordance with another embodiment of the invention is seen generally at 26. The graft 26 of this embodiment includes an inner and outer surface 28 and 30 and is formed from a plurality of fibers indicated generally at 29. As seen in FIG. 3 the graft is formed with two layers of fibers, an inner layer 32 and an outer layer 34. Layer 32 is formed a plurality of hollow fibers, one of which is seen at 36. Unlike the embodiment described above, which included a plurality of hollow fibers 18 positioned circumferentially about the graft 12 axis, the hollow fibers 36 defining the layer 32 of this embodiment are longitudinally arranged substantially parallel to the graft 26 axis. The remainder of the graft 26 is formed from a plurality of solid or hollow fibers, one of which is seen at 38, wound about the longitudinally arranged hollow fibers 36.

It should be noted that the embodiment illustrated in FIGS. 3 and 4 may be prepared entirely from porous hollow fibers. Thus the graft 26 may include a first longitudinally positioned layer of porous hollow fibers encircled by an outer layer of circumferentially or spirally arranged hollow fibers.

As stated, a drug or other suitable composition may be stored within the porous hollow fibers. While many different techniques may be employed for supplying the drug or suitable composition to the hollow fibers one particular advantageous means is to soak the vascular grafts in the desired composition for a predetermined period of time sufficient to allow the composition to be absorbed into the hollow fibers. This is highly dependent upon the viscosity of the composition, and the pore structure of the individual hollow fibers, as well as the pore structure of the fiber matrix forming the vascular graft. However, one of ordinary skill in the art will be able to determine the necessary conditions under which the porous hollow fibers become substantially saturated with the composition.

Figure 5:
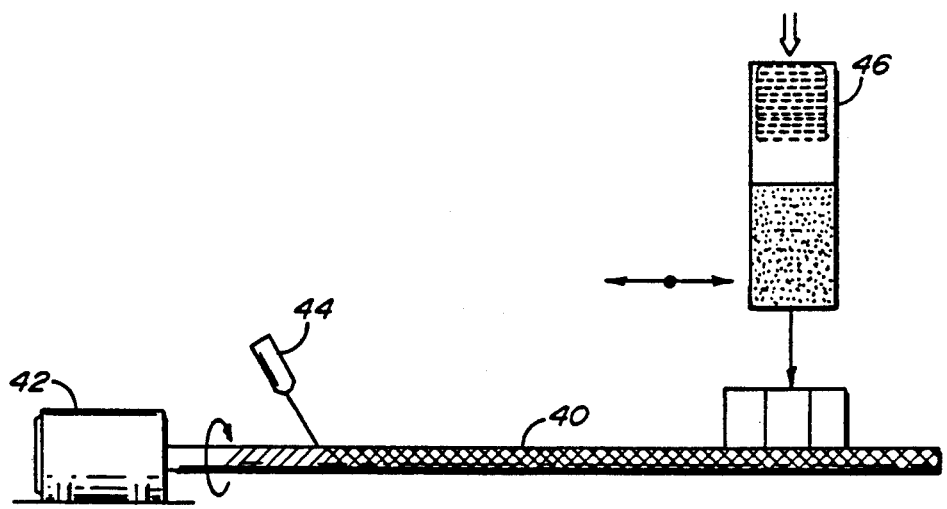
FIG. 5 is a schematic illustration of an apparatus for preparing vascular grafts in accordance with the invention.

As stated above the graft of the invention may be prepared by any suitable method. One particular method is generally illustrated in FIG. 5. This method involves winding the hollow and solid fibers about the outer surface of a rotating mandrel 40. This mandrel 40 is rotated by a motor 42 coupled to one end of the mandrel 40. The mandrel 40 is typically coated with a release agent to allow for the ease in removal of the formed graft. Furthermore, the mandrel 40 may be selectively heated to a desired temperature in order to facilitate the sintering of the graft structure.

The fibers, both solid and hollow, may be preformed, and merely wound about the surface of the mandrel 40. This winding process is performed by a spindle machine, which is generally referenced at 44. A spool and other necessary machinery to deliver the fiber to the spindle machine 44 are not shown. The angle which the fibers are being wound about the mandrel 40 is dependent upon the desired properties for the resulting graft. As is generally known, the angle of fiber winding affects the overall elasticity of the graft, and also controls the overall pore size, as defined by the spacing between adjacent fibers of the resulting graft. Since the present invention utilizes the porosity of the porous hollow fibers to provide the necessary porosity, the exact fiber winding angle is not as critical as in the preparation of presently available grafts. Generally, this winding angle is from about 45 degrees to about 80 degrees.

The illustrated embodiment uses a polymer mixture to facilitate the bonding between adjacent fibers. This polymer mixture is sprayed upon the bundle of fibers wound about the mandrel 40 using the spraying mechanism 46. The thickness of the polymer mixture also depends upon the desired porosity for the graft. That is, the polymer mixture will fill in between the adjacent fibers, thus decreasing the overall porosity of the graft. Generally, the thickness of the polymer solution is dependent upon the rate of spraying of the solution over a given area of the graft, that is, fiber bundle forming the graft. Typically, this spray rate is from about 0.1 cc/min to about 1 cc/min. While any suitable polymer solution may be used which is biocompatible and will function for this purpose, the preferred polymer solution is a solution of polyurethane in tetrahydrofuran. This solution is sprayed at a rate of 0.5 cc/min over the fiber matrix which is wound about the mandrel.

It should be noted that other methods may be substituted for the use of the polymer solution to adhere or fix the plurality of fibers together. These other types of methods may include partial melting or sintering of the fibers after such fibers are wound about the mandrel. The only disadvantage in heating the fibers to fix their respective position, is that this results in melting the fibers which may collapse or obstruct the passageway through the hollow fibers.

Another embodiment of the invention is which the hollow fibers are coated with a biodegradeable composition. The biodegradable coating composition initially seals, or partially seals the pores of the hollow fibers. After the vascular graft is implanted, this coating composition will slowly dissolve. The result is that the porosity of the graft gradually increases until the coating composition is entirely dissolved. The benefit of this gradual increase in porosity is two fold. First, immediately after graft implantation it is desirable to have as small a pore size as possible. This is beneficial to reduce bleeding during the initial healing process. As the healing process continues the larger the pore size the more tissue in-growth occurs. Thus the use of a biodegradable coating composition provides for the initial small pore size with a gradually increase as the coating composition dissolves.

The second benefit derived from the use of this type of coating composition is the gradually release of any drug contained within the hollow fibers. That is, as the coating composition dissolves the pore size increases, thus increasing the release of the drug.

While any suitable biodegradable material may be used the more preferred coating composition materials are poly(L-lactic acid), a copolymer of D,L-lactic acid and glycine, and polyglycolic acid.

Furthermore, the coating composition may be applied in any suitable manner, e.g. by dipping, spraying or coating the coating composition directly upon the fibers. Preferably, the coating composition is applied as a co-extrusion. This is generally performed by using an extruder having two polymer feeding ports. The fiber forming polymer will be fed through the inner feeding ports to form the fibers, with the biodegradable polymer being fed through the outer feeding ports to form the coating.

It should further be noted that the vascular grafts prepared in accordance with the invention may incorporate other modifications generally found with available grafts. For example, the vascular grafts may be formed with one or more O-rings positioned along the length of the graft. These O-rings provide the graft with increased reinforcement, and provide the graft with kink-resistance. The O-rings may be separate structures embedded into the outer layer of the graft, or may be integrally formed in the graft by the appropriate control of the fiber winding to form an O-ring like structure.

While the preferred embodiments have been described, various modifications and substitutions may be made thereto without departing from the scope of the invention. Accordingly, it is to be understood that the invention has been described by way of illustration and not limitation.

What is claimed is:

1. A vascular graft comprised of a tubular body formed from a porous, biocompatible material and having an inner surface defining an open passageway through which a fluid can pass, said tubular body including a layer of porous hollow fibers positioned along said inner surface.

2. An implantable vascular graft comprised of a tubular body formed from a porous, biocompatible material and having an inner surface defining an open passageway through which a fluid can pass, said tubular body including porous hollow fibers with at least a portion of said porous hollow fibers forming at least a portion of said inner surface.

3. The implantable vascular graft of claim 2 wherein said porous hollow fibers form said inner layer of said vascular graft, which inner layer defines said open passageway.

4. The implantable vascular graft of claim 3 wherein said vascular graft further includes an outer layer formed from fibers.

5. The implantable vascular graft of claim 2 wherein said vascular graft is comprised essentially of all porous hollow fibers.

6. The implantable vascular graft of claim 4 wherein said fibers forming said outer layer are solid.

7. The implantable vascular graft of claim 4 wherein said fibers forming said outer layer are porous and hollow.

8. The implantable vascular graft of claim 4 wherein said porous hollow fibers forming said inner layer are arranged circumferentially about an axis of said graft.

9. The implantable vascular graft of claim 4 wherein said porous hollow fibers forming said inner layer are arranged substantially parallel to an axis of said graft.

10. The implantable vascular graft of claim 8 wherein said vascular graft is comprised essentially of all porous hollow fibers.

11. The implantable vascular graft of claim 8 wherein said fibers forming said outer layer are solid.

12. The implantable vascular graft of claim 8 wherein said fibers forming said outer layer are porous hollow fibers.

13. The implantable vascular graft of claim 9 wherein said vascular graft is comprised essentially of all porous hollow fibers.

14. The implantable vascular graft of claim 9 wherein said fibers forming said outer layer are solid.

15. The implantable vascular graft of claim 9 wherein said fibers forming said outer layer are porous hollow fibers.

16. The vascular graft of claim 10 wherein at least some of said porous hollow fibers are coated with a biodegradable polymer.

17. The vascular graft of claim 11 wherein at least some of said porous hollow fibers are coated with a biodegradable polymer.

18. The vascular graft of claim 12 wherein at least some of said porous hollow fibers are coated with a biodegradable polymer.

19. The vascular graft of claim 8 wherein at least some of said porous hollow fibers forming said vascular graft are filled with a drug composition.

20. The vascular graft of claim 9 wherein at least some of said porous hollow fibers forming said vascular graft are filled with a drug composition.

21. The vascular graft of claim 10 wherein at least some of said porous hollow fibers forming said vascular graft are filled with a drug composition.

22. The vascular graft of claim 11 wherein at least some of said porous hollow fibers forming said vascular graft are filled with a drug composition.

23. The vascular graft of claim 16 wherein at least some of said porous hollow fibers forming said vascular graft are filled with a drug composition.

24. The vascular graft of claim 17 wherein at least some of said porous hollow fibers forming said vascular graft are filled with a drug composition.

25. The vascular graft of claim 8 wherein at least some of said porous hollow fibers are filled with an inert gas.

26. The vascular graft of claim 9 wherein at least some of said porous hollow fibers are filled with an inert gas.

27. The vascular graft of claim 10 wherein at least some of said porous hollow fibers are filled with an inert gas.

28. The vascular graft of claim 11 wherein at least some of said porous hollow fibers are filled with an inert gas.

29. The vascular graft of claim 16 wherein at least some of said porous hollow fibers are filled with an inert gas.

30. The vascular graft of claim 17 wherein at least some of said porous hollow fibers are filled with an inert gas.

* * * * *